(12) United States Patent
Booth

(10) Patent No.: US 8,707,806 B2
(45) Date of Patent: Apr. 29, 2014

(54) SAMPLING AND MONITORING OF PARTICULATE SUSPENSION MATERIAL

(75) Inventor: Robert Booth, Ashtonfield (AU)

(73) Assignee: Bloomfield Collieries Pty Limited (AU)

( * ) Notice: Subject to any disclaimer, the term of this patent is extended or adjusted under 35 U.S.C. 154(b) by 689 days.

(21) Appl. No.: 12/225,616

(22) PCT Filed: Mar. 21, 2007

(86) PCT No.: PCT/AU2007/000345
§ 371 (c)(1),
(2), (4) Date: Apr. 6, 2009

(87) PCT Pub. No.: WO2007/109833
PCT Pub. Date: Oct. 4, 2007

(65) Prior Publication Data
US 2009/0217778 A1 Sep. 3, 2009

(30) Foreign Application Priority Data
Mar. 28, 2006 (AU) ................................ 2006901578

(51) Int. Cl.
*G01N 1/00* (2006.01)
(52) U.S. Cl.
USPC ....................................................... 73/863.23
(58) Field of Classification Search
None
See application file for complete search history.

(56) References Cited

U.S. PATENT DOCUMENTS

| | | | |
|---|---|---|---|
| 3,690,184 A * | 9/1972 | Chadenson | 73/438 |
| 3,979,669 A | 9/1976 | Godin | |
| 4,201,082 A * | 5/1980 | Dockhorn et al. | 73/152.42 |
| 4,727,758 A | 3/1988 | Murdock | |
| 5,454,912 A | 10/1995 | Dougherty | |
| 5,602,348 A * | 2/1997 | Takakarhu et al. | 73/864.81 |
| 5,641,894 A * | 6/1997 | Hosokawa | 73/64.56 |
| 7,658,094 B2 * | 2/2010 | Brumboiu et al. | 73/64.56 |
| 2005/0150841 A1 * | 7/2005 | Ferguson | 210/741 |

FOREIGN PATENT DOCUMENTS

| | | |
|---|---|---|
| EP | 0455333 A2 | 11/1991 |
| JP | 06-285500 A | 10/1994 |
| JP | 2001-281241 A | 10/2001 |
| SU | 1569557 A | 6/1990 |
| WO | WO 01/67068 A3 | 9/2001 |
| WO | WO 03/069313 A1 | 8/2003 |

* cited by examiner

Primary Examiner — Robert R Raevis
(74) Attorney, Agent, or Firm — Morriss O'Bryant Compagni

(57) ABSTRACT

Apparatus for use in measuring properties of media formed from a particulate suspension. The apparatus includes a media sampler coupled to feed pipes to allow media to flowing therethrough to be sampled and a connector for coupling the media sampler to a sensor for sensing properties of the sampled media.

38 Claims, 11 Drawing Sheets

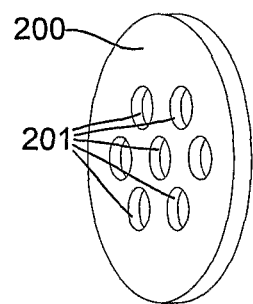
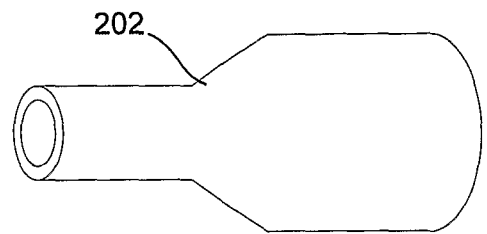
Fig. 2C  Fig. 2D
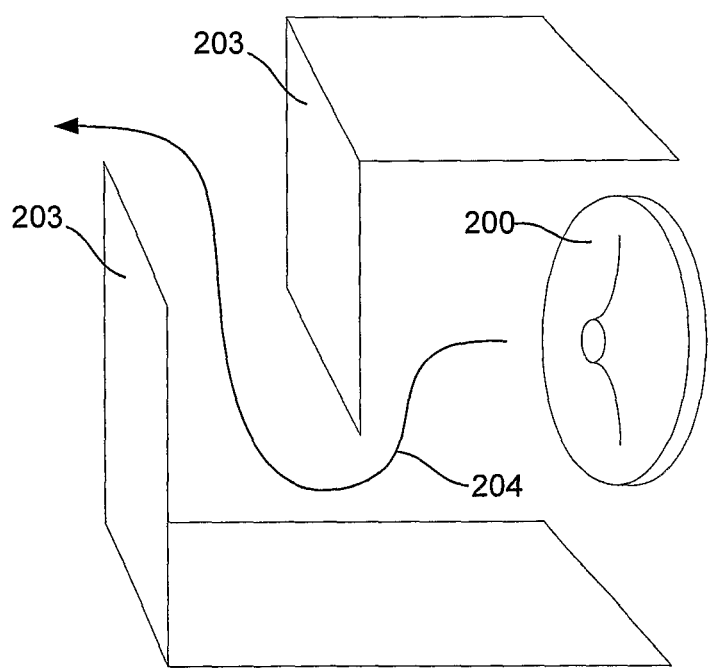
Fig. 2E

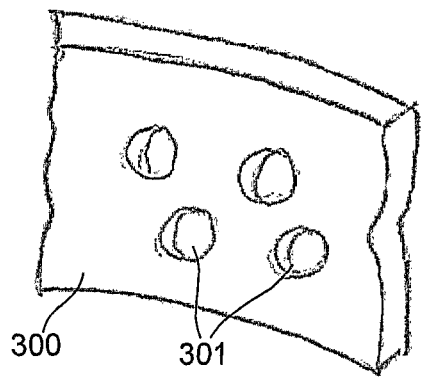
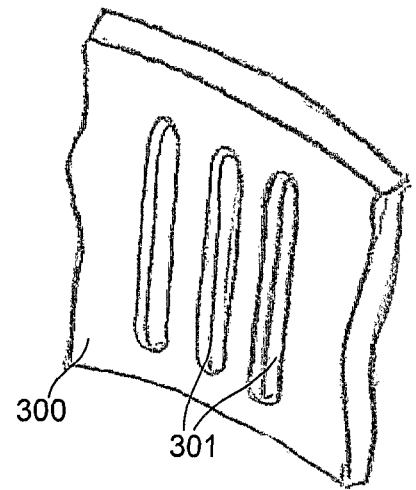
Fig. 3A Fig. 3B
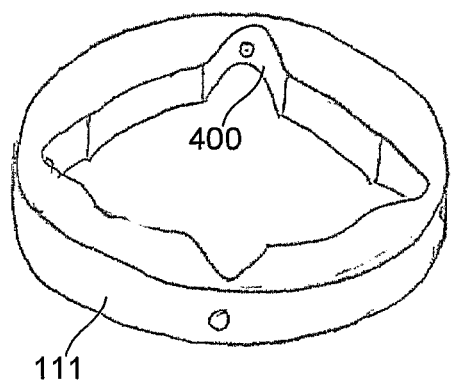
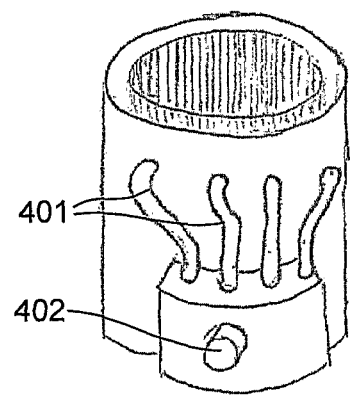
Fig. 4A Fig. 4B

SAMPLING AND MONITORING OF PARTICULATE SUSPENSION MATERIAL

BACKGROUND OF THE INVENTION

The present invention relates to apparatus for monitoring properties of a particulate suspension, and in particular, to apparatus for monitoring the density of flowing slurry.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Slurry is a term used to refer to fluids containing a high concentration of suspended solids. Slurries are often used for allowing particulate solid materials to be transported and/or processed in a fluidised form.

In many circumstances it is important that the properties, such as the density of a flowing slurry are known, for example to ensure that associated equipment is operated correctly, and within defined safety and/or operating parameters. This is particularly the case when slurry is supplied to a hydro cyclone for separation into its constituent fluid and solid components.

However, existing density sensors are typically only of limited use. For example, most common devices are nucleonic devices that are not only expensive, but are also perceived as dangerous and consequently, are not favoured by operators. As a result, there are moves to eliminate such sensors in many jurisdictions, and it is therefore necessary for a replacement to be developed.

Existing mechanical devices for measuring the density experience problems with control and accuracy due to their location in the process circuit, primarily due to the high pressures involved in slurry flow and the existence of large particles.

These problems have led to variances in measured density that are greater than the accuracy of the devices that operate in the circuit. As accurate density control is required in order to attain maximum efficiency from hydro cyclones and other equipment, this causes consequent problems and inefficiencies in system operation.

SUMMARY OF THE PRESENT INVENTION

In a first broad form the present invention provides apparatus for use in measuring properties of media formed from a particulate suspension, the apparatus including:
  a) a media sampler, the media sampler being coupled to feed pipes to allow media to flowing therethrough to be sampled;
  b) a connector for coupling the media sampler to a sensor for sensing properties of the sampled media.

Typically the media sampler is formed from:
  a) a jacket coupled to the feed pipes;
  b) an outlet; and,
  c) an element having one or more apertures, the element being arranged within the jacket such that as media flows therethrough, at least some of the media passes through the one or more apertures and into the outlet.

Typically the element is formed from a mesh.

Typically the mesh has apertures of less than 2 mm diameter, and preferably of approximately 1 mm or 0.5 mm.

Typically the element and the jacket are substantially cylindrically shaped.

Typically wherein the jacket includes an access door to allow the element to be removed from the jacket.

Typically the connector includes a pressure reducing outlet for at least one of:
  a) reducing the flow pressure of the sampled media; and,
  b) providing a quiescent or laminar flow of sampled media to the sensor.
  c) preventing material blocking a surface of the element; and,
  d) creating a pressure differential between the surface of the element and a chamber.

Typically the pressure reducing outlet reduces the pressure of the sampled media to substantially atmospheric pressure.

Typically the pressure reducing outlet is formed from at least one of:
  a) a plate including one or more apertures; and,
  b) one or more baffles defining a convoluted flow path.

Typically the connector includes a valve for selectively controlling the flow of sampled media.

Typically the valve is positioned between the media sampler and the pressure reducing outlet.

Typically the sensor is a differential pressure sensor.

Typically the sensor is formed from:
  a) a sensing tube having an inlet coupled to the connector;
  b) an outlet for returning sampled media; and,
  c) at least two pressure sensors position along the sensing tube to thereby determine the pressure of sampled media at different positions.

Typically the sensor further includes an overflow pipe for returning excess sampled media.

Typically the sensor further includes a chamber for coupling the sensing tube to the connector.

Typically the chamber includes:
  a) a first outlet for coupling the chamber to the sensing tube; and,
  b) a second outlet for coupling the chamber to an overflow pipe.

Typically the first and second outlets are relatively positioned such that sampled media will only flow through the second outlet when overflow occurs.

BRIEF DESCRIPTION OF THE DRAWINGS

An example of the present invention will now be described with reference to the accompanying drawings, in which:

FIGS. 2A to 2E are schematic diagrams of examples of pressure reducing outlets;

FIGS. 3A and 3B are schematic diagrams of example elements;

FIGS. 4A and 4B are schematic diagrams of example jackets;

DETAILED DESCRIPTION OF THE PREFERRED EMBODIMENTS

Figure 1A:
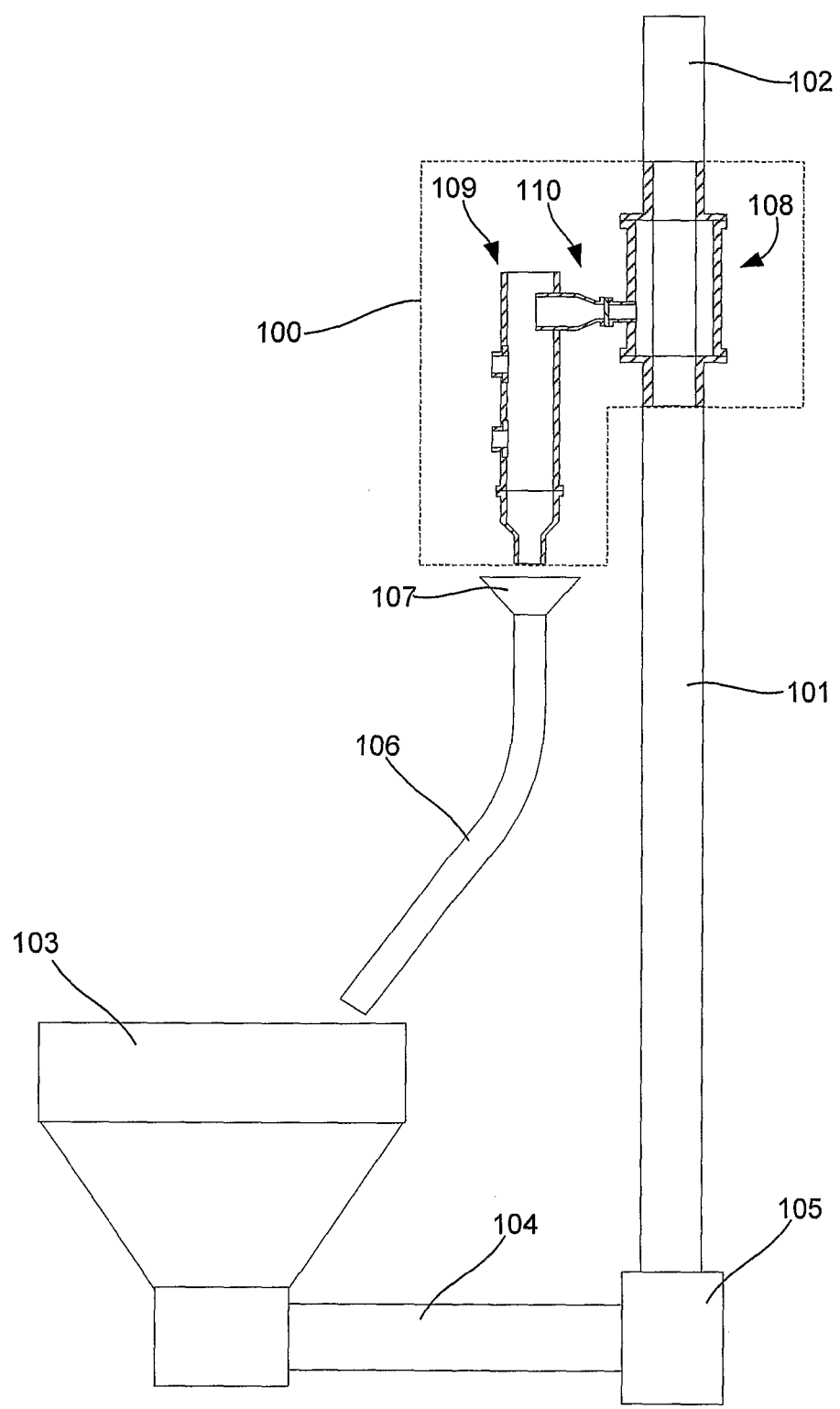
FIG. 1A is a schematic diagram of an example of apparatus for measuring the properties of a media.

An example of apparatus for measuring the properties of a media, such as slurry, will now be described with reference to FIGS. 1A to 1C. This example focuses on the measurement of density, but it will be appreciated that other properties of the media could be measured.

In this example, the apparatus is formed from a measuring device 100, which is coupled to pipes 101, 102 to allow properties of slurry therein to be measured. The measuring device 100 includes a media sampler 108, coupled to a measurement chamber 109, via a connector 110. This allows the measuring device 100 to sample the slurry in the pipe 101, and then determine the density of the sampled slurry, as will be explained in more detail below.

In one example, the measuring device 100 is used to measure the density of slurry provided to a hydro-cyclone via the pipe 102. In this example, it is typical for the slurry to be supplied from a dense media sump 103, via a pipe 104 and a pump 105, to the pipe 101. The sampled slurry can then be returned to the dense media sump 103, via a collector 107 and pipe 106, as shown. However, it will be appreciated however that this is for the purpose of example only and any configuration may be used.

The measuring device 100 will now be described in more detail with reference to FIGS. 1B and 1C.

In this example, the media sampler 108 is formed from a jacket 111, having flanges 112, 113, for coupling to flanges 114, 115, provided on the pipes 101, 102. The media sampler 108 includes an element 116, which includes a number of apertures to allow the slurry to be sampled.

The jacket 111 is coupled to the connector 110, which is formed from an outlet 117, having a flange 118 that is coupled to a pressure reducing outlet 119. The pressure reducing outlet 119 is then coupled to a sensor inlet 120 via a flange 121.

The measurement chamber 109 is formed from a sensing tube 122 having a flange 123 for coupling the sensing tube 122, via a flange 124, to an outlet 125. The sensing tube 122 includes sensor mounts 126, 127, which are used to mount pressure sensors 128, 129, in use. An overflow pipe 130 is also typically provided as shown in FIG. 1C.

Operation of the measuring device will now be described. In particular, slurry flows along the pipe 101, as shown by the arrow 140, and enters the media sampler 108. The element 116, which is described in more detail below, includes apertures that allow material to pass through the element 116, as shown by the arrows 141, and flow into the outlet 117. The material then passes through the pressure reducing outlet 119, through the sensor inlet 120, and into the sensing tube 122, as shown by the arrow 142.

The pressure reducing outlet 119, which will be described in more detail below, reduces the pressure of the flow, so that properties of the material flowing through the sensing tube 122 may be more accurately measured. In one example, the pressure reducing outlet 119 attenuates the pressure to atmospheric pressure so that the flow through the sensing tube 122 is a low velocity, quiescent laminar flowing slurry in suspension, thereby allowing density or another analysis to be performed.

The pressure reducing outlet 119 also helps control the differential pressure drop between the surface of the sampling element 116 and the jacket 111. Creating a pressure differential between the surface of the element 116 and the sensing tube 122, or any other collection or material chamber, allows the removal of pegged material from the surface of the sampling element 116 that otherwise would normally peg and hence block the surface apertures of the sampling element 116.

The pressure reducing outlet 119 is also configured to control the flow rate of the sampled media, so that the sensing tube 122 maintains at least a minimum level of material, which is above the position of the sensors 128, 129, as shown at 143.

Figure 1B:
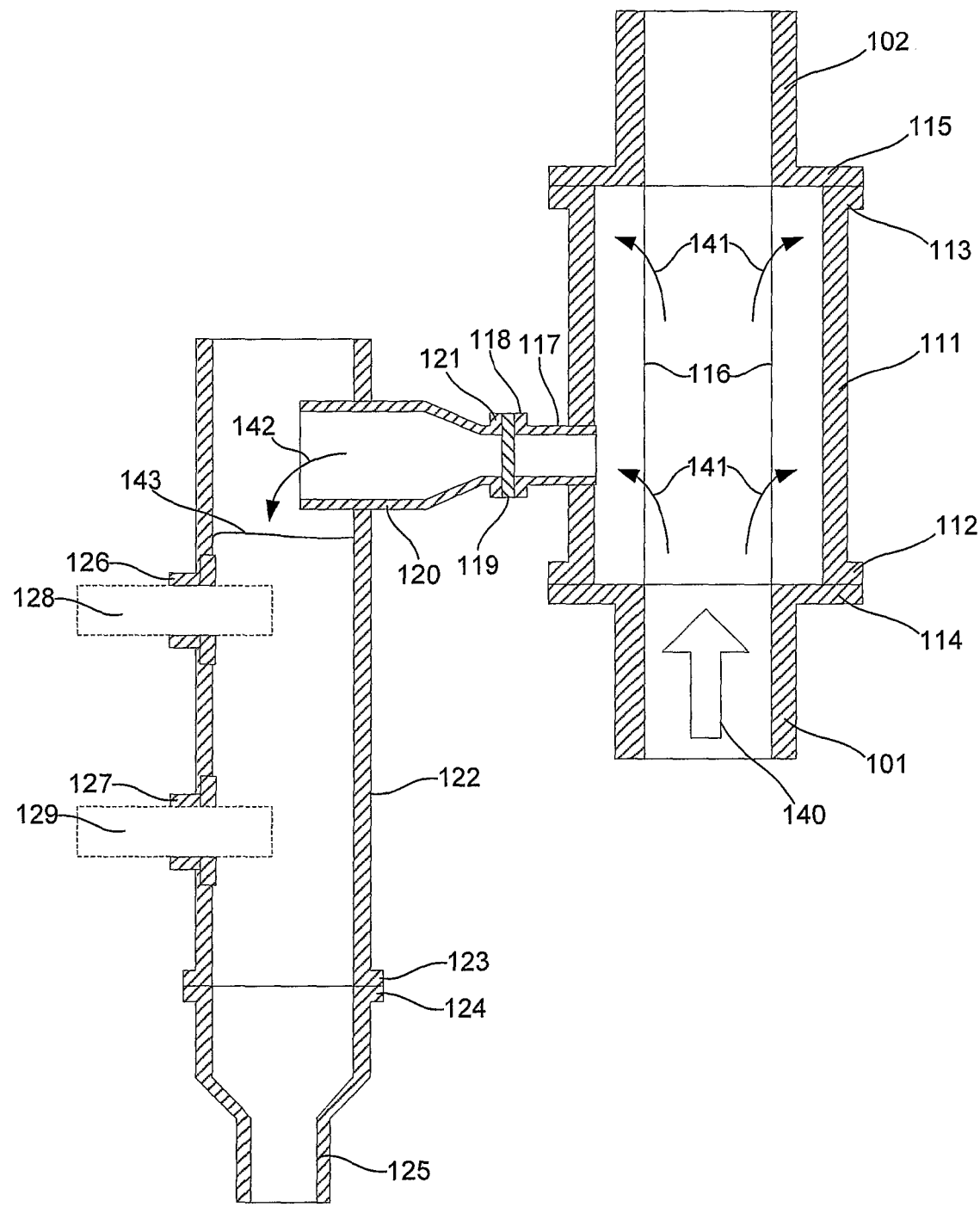
FIG. 1B is a cross sectional side view of an example of the density sensor of FIG. 1A.
Figure 1C:
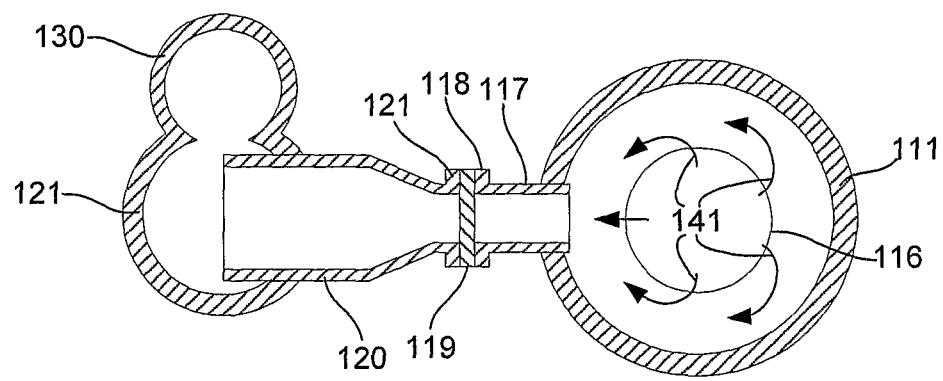
FIG. 1C is a cross sectional plan view of an example of the density sensor of FIG. 1A.

To help achieve this, as shown in FIG. 1C, an overflow pipe 130 can be coupled to the sensing tube 122. This allows an excess of material to be supplied to the sensing tube 122, to ensure the minimum level 143 is maintained, with any excess being drained, via the overflow pipe 130, to ensure the sensing tube 122 does not overflow. The overflow pipe then returns the excess material to the collector 107, allowing it to be returned to the dense media sump 103.

In any event, the difference between the pressure measured by each of the sensors 128, 129, and the relative vertical height between the sensors 128, 129 can then be used to calculate a density, representative of the density of the slurry in the pipes 101, 102.

In this regard, the relationship between the measured density and the density of the slurry in the pipes 101, 102 may not be a one-to-one relationship due to a number of factors such as the size fraction of material sampled by the media sampler 108. However, any such relationship can be determined, either by measurement or calculation, allowing the density in the pipes 101, 102 to be accurately determined.

As described above, the purpose of the pressure reducing outlet 119 is to reduce the flow pressure to allow accurate measurement of the density and control the differential pressure drop between the surface of the sampling element 116 and the jacket 111. This can be achieved using a number of different arrangements, as shown for example in FIGS. 2A to 2E.

Figure 2A:
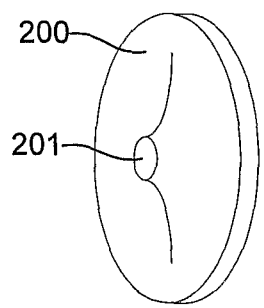
Figure 2B:
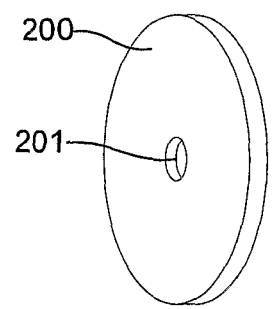

In the example shown in FIGS. 2A and 2B, the pressure reducing outlet is formed from a plate 200 having an orifice, or aperture 201. The size of the aperture 201 can be selected to vary the degree of pressure attenuation and sample rate, allowing the system to be used with a range of different pressures within the pipes 101, 102.

However, any element that allows pressure attenuation to be achieved may be used. Thus, for example, as shown in FIG. 2C a number of apertures 201 may be used. Alternatively, instead of using a plate 200, a tapered tube 202 can be used as shown in FIG. 2D.

Additionally, and/or alternatively, the above described elements may be used in conjunction with a series of baffles 203, which define a convoluted flow path 204, so that the pressure is attenuated in a sequence of steps, or pressure bands.

It will be appreciated that the pressure reducing outlet 119 is typically formed from wear resistant materials to prevent wear and hence an alteration of the pressure attenuation in use.

An example of the element 116 will now be described in more detail. In particular, as mentioned above the element 116 includes apertures allowing a portion of the material flowing through the pipes 101, 102, to be diverted into the outlet 117. In one example, this is achieved using a wedge wire screen with the same inside diameter as the feed pipe 101. In one example, the wire screen is approximately 500 mm long and having apertures of approximately 1 mm in diameter. This helps ensure even flow of the slurry through the media sampler and reduce wear on the element.

It will also be appreciated that any suitable element may be used. As shown for example in FIGS. 3A and 3B, the element could be formed from a solid member 300, such as a pipe, having a number of apertures 301 therein.

In either case, the form, number, size and shape of the apertures may be varied to allow different particles to pass therethrough. Thus, the aperture properties may be selected based on the type of slurry to be sampled.

Thus, different aperture sizes and shapes may be used however depending on a range of factors, such as the nature of the material being sampled, material flow rates, or the like. In general, the apertures are formed from holes or elongate slots, and have a diameter, or dimensions of less than 2 mm, and more typically of approximately 1 mm or 0.5 mm. It will be appreciated however, that these size ranges and shapes are for the purpose of example only and are not intended to be limiting.

Additionally the shape of the element 116 is typically selected so the profile of the element matches that of the material conveying means. In this example, the shape of the element is therefore based on the shape of the pipes 101, 102. Thus, as the pipes 101, 102 have a circular cross sectional shape, the element 116 is selected to have an overall cylindrical shape. However, this is not essential, and generally any shape may be used, although preferably, the shape is selected to correspond to the profile of the pipes 101, 102, or any other material conveying means with which the sensing system is to be used.

Similarly, it will be appreciated that the jacket may be of any suitable form. Thus, in the example described above, the jacket is formed form a 400 NB pipe which surrounds and encloses the element. However, as shown in FIGS. 4A and 4B, alternative designs could be used. Thus, as shown in FIG. 4A, the internal shape 400 of the jacket 111 can be of any form and is not restricted to a circular shape. Thus, for example, the cross-sectional shape of the jacket 111 would typically be selected to correspond to the shape of the pipes 101, 102, although again other shapes would typically be used with other material conveying means, as appropriate.

Additionally, the jacket may include a number of outlets 401, which are combined into a single outlet port 402, which is in turn coupled to the pressure reducing outlet 119. This helps ensure even flow of material from the cavity between the element 116 and the jacket 111.

A second example of apparatus for measuring media properties will now be described with reference to FIGS. 5A to 5E.

In this example, the apparatus includes similar components to those shown in FIGS. 1A to 1C, with these similar components being designated with reference numerals increased by 400. Thus, in this example, the apparatus includes a media sampler 508, which is similar to the media sampler 108 of FIG. 1A.

In this example, the media sample at 508 includes an aperture 511A provided in the jacket 511, allowing the element 516 to be inserted into and removed from the media sampler 508. The media sampler 508 also includes an access door in the form of a locking plate 540, formed from a backing member 541 having handles 542 mounted thereto. The backing member 541 also includes a mounting 543 for receiving the element 516. Accordingly, by coupling the element 516 to the mounting 543, and then attaching the locking plate 540 to the jacket 511, this operates to support the element 516 in the correct location within the media sampler 508. This also allows the element 516 to be easily removed from the media sampler 508, for example to allow the element 516 to be cleaned or replaced.

As in the previous example, the media sampler 508 has an outlet 517 having a flange 518 to allow it to be connected to downstream components. In this example the flange 518 is coupled to a valve 550 via a flange 552. The valve 550 includes a control nut 551 which allows the valve opening to be controlled thereby the flow of material through the valve 550, and hence through the connector 510 to be controlled. The valve 550 also includes a flange 553, which in use is coupled to the pressure reducing outlet 519. This allows the flow of material to be halted in the event that measurements are not required, as well as allowing the flow of material to the pressure reducing outlet to be controlled, thereby ensuring the pressure reducing outlet functions correctly.

In this example, the measurement chamber 509 includes a sensor inlet 520 coupled to the pressure reducing outlet 519 via a flange 521. The sensor inlet 520 feeds into a material chamber shown generally at 560. The material chamber 560 includes two outlets 561, 562 which couple respectively to a sensing tube 522 and an overflow tube 530. The sensing tube 522 is of a similar configuration to the sensing tube 122 shown in FIGS. 1A to 1C, and therefore includes mounts 526, 527 for receiving sensors such as pressure sensors, flow sensors, or the like.

Figure 5A:
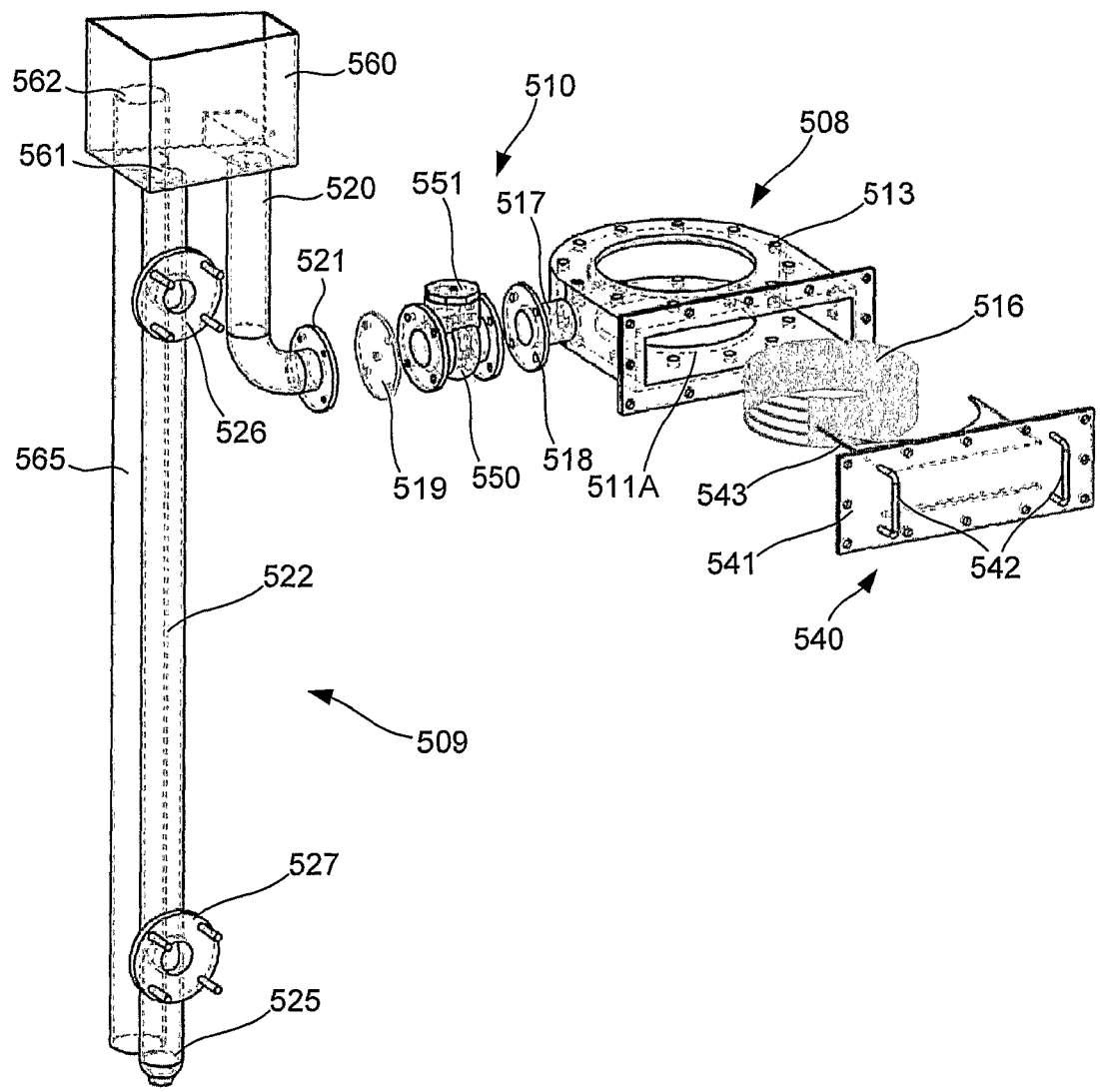
FIGS. 5A to 5E are schematic diagrams of a second example of apparatus for measuring the properties of a media; and, FIGS. 6A to 6C are schematic diagrams of a third example of apparatus for measuring the properties of a media.
Figure 5B:
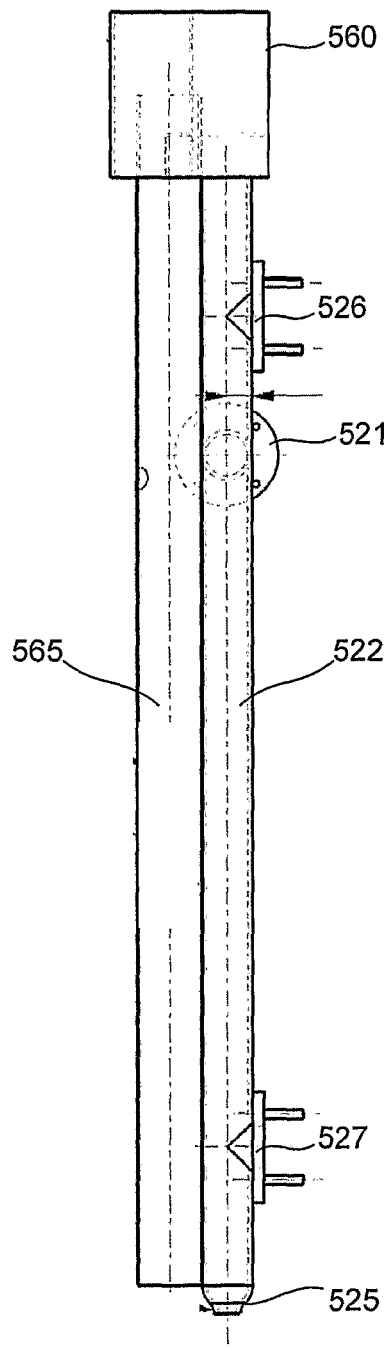
Figure 5C:
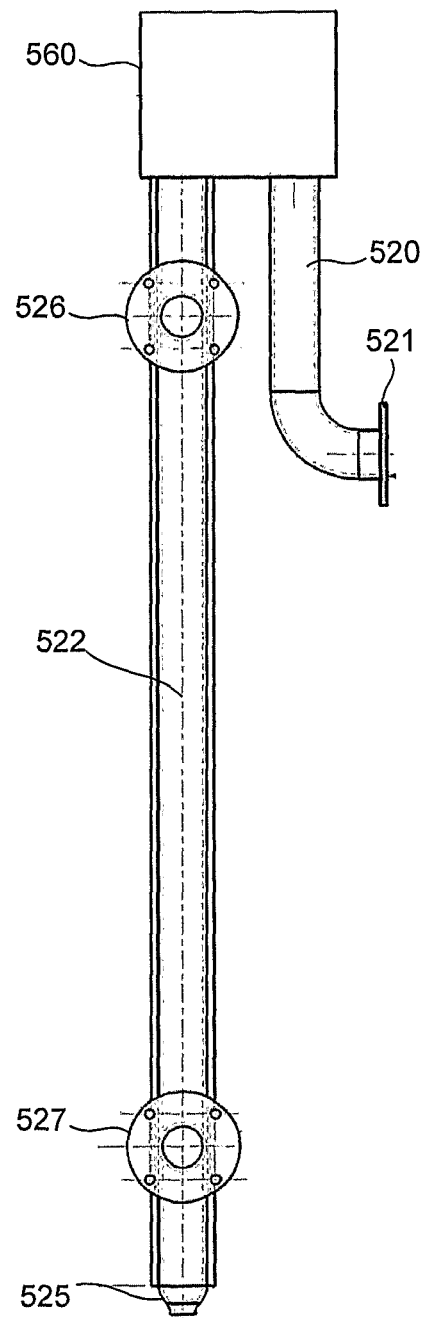
Figure 5D:
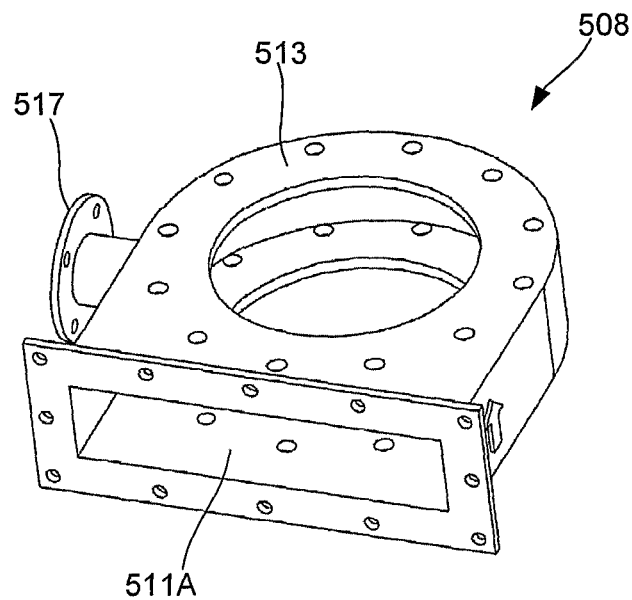
Figure 5E:
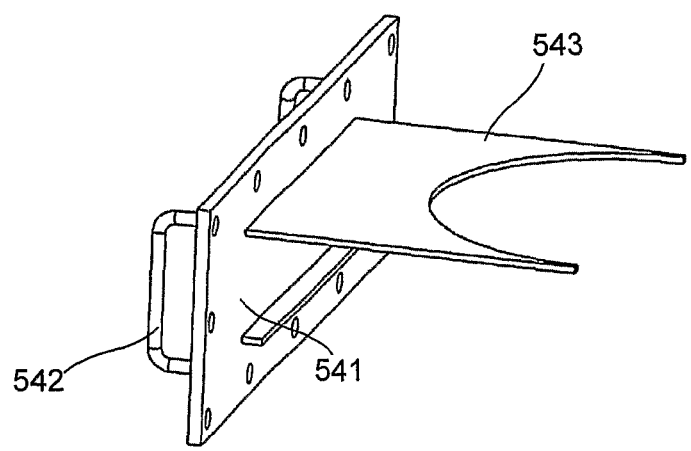

In this example, as shown in FIG. 5A the first outlet 561 to the sensing tube 522 is positioned at a lower level than the second outlet 562 for the overflow tube 530. As a result of this, in use, media flowing through the sensor inlet 520, collects in the chamber 560 and flows through the first outlet 561 into the sensing tube 522. In the event that the flow of material into the chamber 560 is greater than can be accommodated by the sensing tube 522, the media level will rise until it is above the level of the second outlet 562. As a result, excess material flows through the overflow tube 565, ensuring that the chamber 560 does not overfill.

It will be appreciated by persons skilled in the art that this ensures a constant flow of media via the chamber 560 into the sensing tube 522, whilst ensuring that the chamber 560 does not overfill or clog. The presence of the chamber 560 therefore helps ensure that flow of material within the sensing tube 522 is separated from the high velocity flow exiting the pressure reducing outlet 519, and hence that the flow of material is quiescent. This vastly enhances the reliability and accuracy of the measurement procedure.

In addition to this, the use of the locking plate 540 allows the element 516 to be removed and replaced or cleaned in the event that it becomes clogged, as well as allowing different elements to be used for different media flows as appropriate.

Figure 6A:
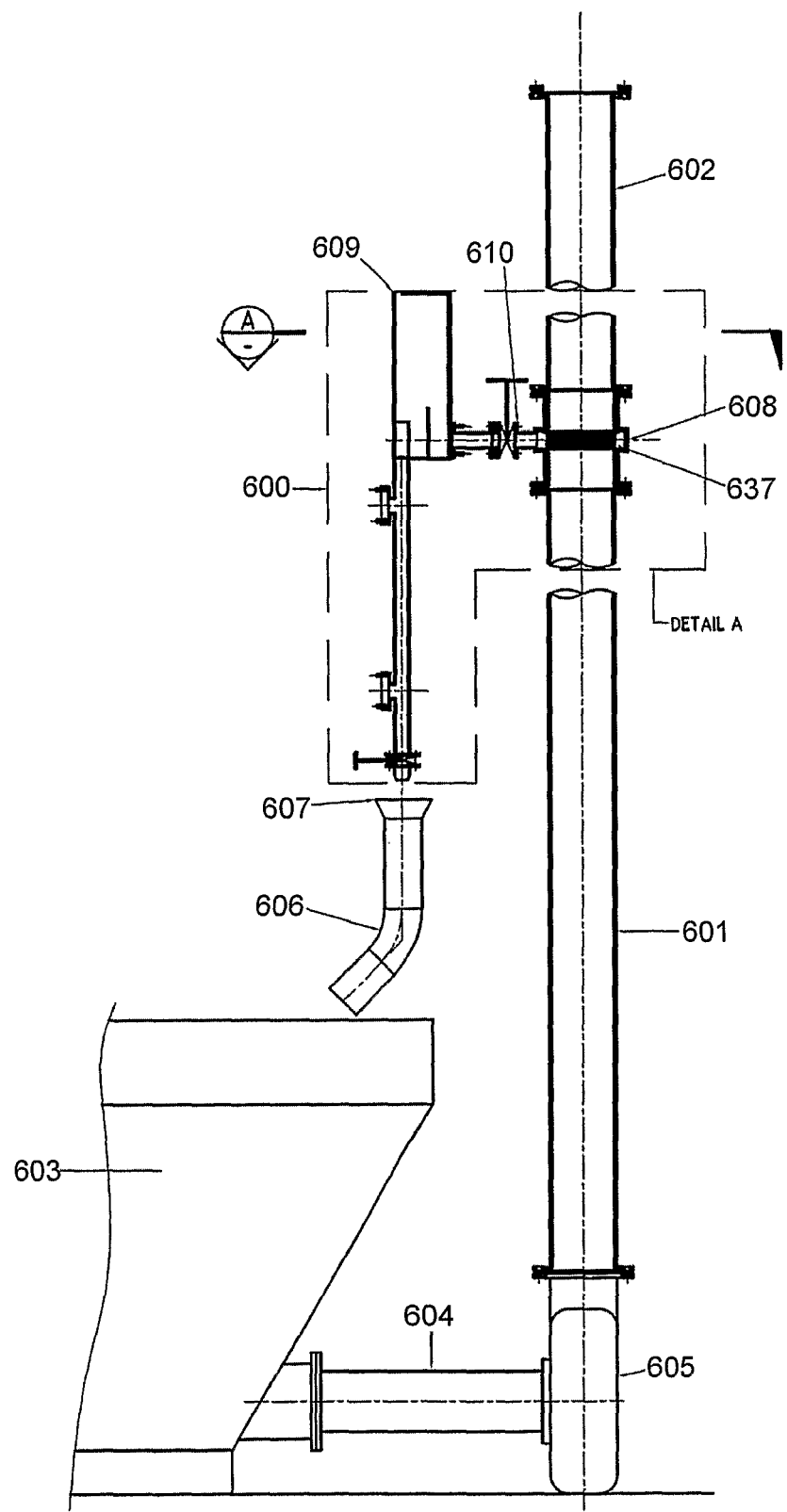

A third example of apparatus for measuring media properties will now be described with reference to FIGS. 6A to 6C.

In this example, the apparatus includes a measuring device 600 coupled to pipes 601, 602 to allow properties of slurry therein to be measured. The measuring device 600 includes a media sampler 608, coupled to a measurement chamber 609, via a connector 610. As in the example of FIG. 1A, the slurry is typically supplied from a dense media sump 603, via a pipe 604 and a pump 605, to the pipe 601. The sampled slurry can then be returned to the dense media sump 603, via a collector 607 and pipe 606, as shown.

In this example, the media sampler 608 is formed from a jacket 611, having flanges 612, 613, for coupling to flanges 614, 615, provided on the pipes 601, 602. The media sampler 608 includes an element 616, which includes a number of apertures to allow the slurry to be sampled. The media sampler includes an access door 637 to allow the element 616 to be removed and/or replaced.

The jacket 611 is coupled to the connector 610, which is formed from an outlet 617, having a flange 618 connected to a knife gate valve 619 that is coupled to a pressure reducing outlet 620. The pressure reducing outlet 620 having a flange 621 is then coupled to a measurement chamber via inlet 622 having a flange 623.

The measurement chamber 609 is formed from a collector chamber 625 having a flange 623 for coupling the inlet tube 622, to the sensing tube 626. The sensing tube 626, includes sensor mounts 627, 628, which are used to mount pressure sensors 629, 630. Flange 631 connects an adjustable orifice 632 to the sensor tube 626. Flange 633 connects outgoing pipe 634 to the sensor tube 626. An overflow pipe 636 is also typically provided as shown in FIG. 6C.

Operation of the measuring device will now be described. In particular, slurry flows along the pipe 601, as shown by the arrow 640, and enters the media sampler 608. The element 616, which is described in more detail below, includes apertures that allow material to pass through the element 616, as shown by the arrows 641, and flow into the outlet 617. The material then passes through the pressure reducing outlet 620, through the inlet 622, and into the measurement chamber 625, as shown by the arrow 642.

The pressure reducing outlet 620, which will be described in more detail below, reduces the pressure of the flow, so that properties of the material flowing through the sensing tube 635 may be more accurately measured. In one example, the pressure reducing outlet 620 attenuates the pressure to atmospheric pressure so that the flow through the sensing tube 626 is a low velocity laminar flowing slurry in suspension, thereby allowing density or another analysis to be performed.

The pressure reducing outlet 620 creates a pressure differential between the surface of the element and the collection chamber, thus allowing the removal of pegged material from the surface of the sampling element that would normally peg the surface apertures of the sampling element. It is also configured to control the flow rate of the sampled media, so that the adjustable orifice 632 maintains at least a minimum level of material, which is above the position of the sensors 629, 630, as shown at 643.

Figure 6B:
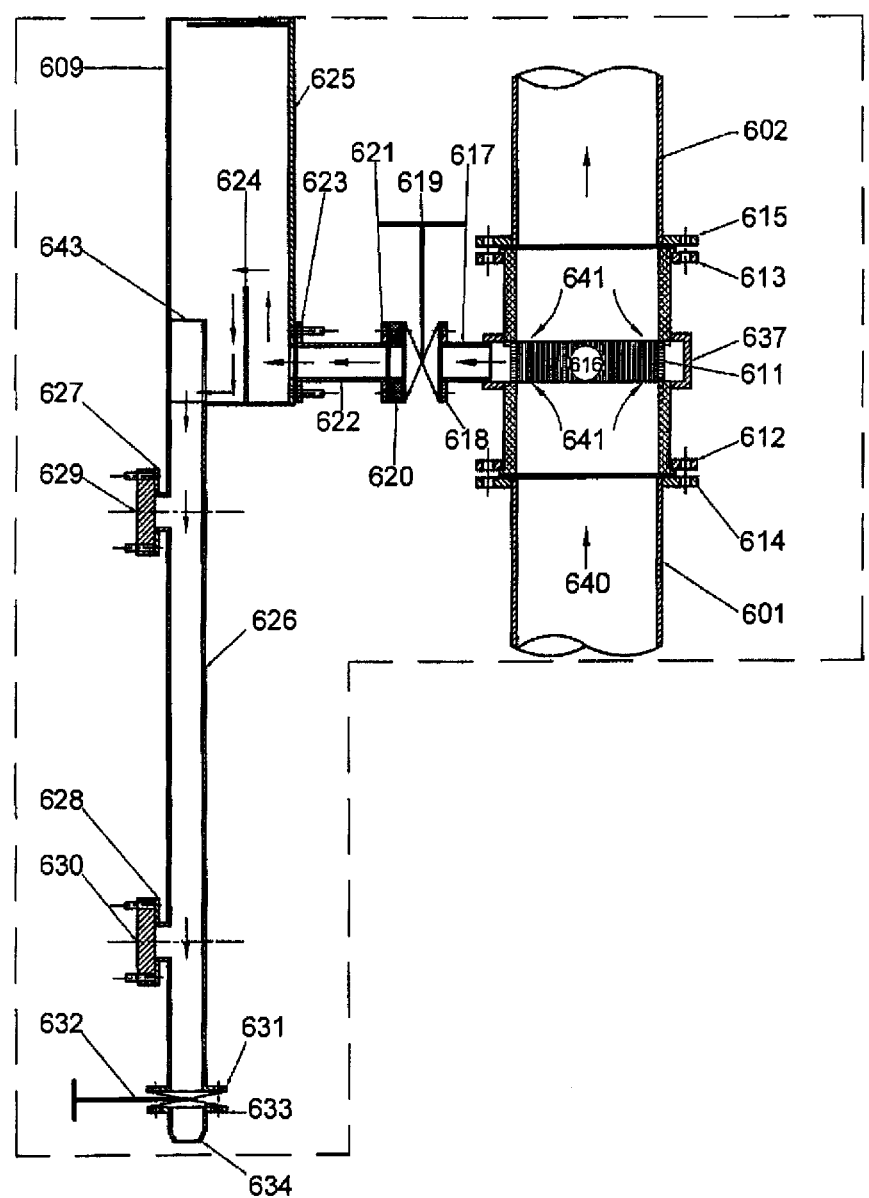
Figure 6C:
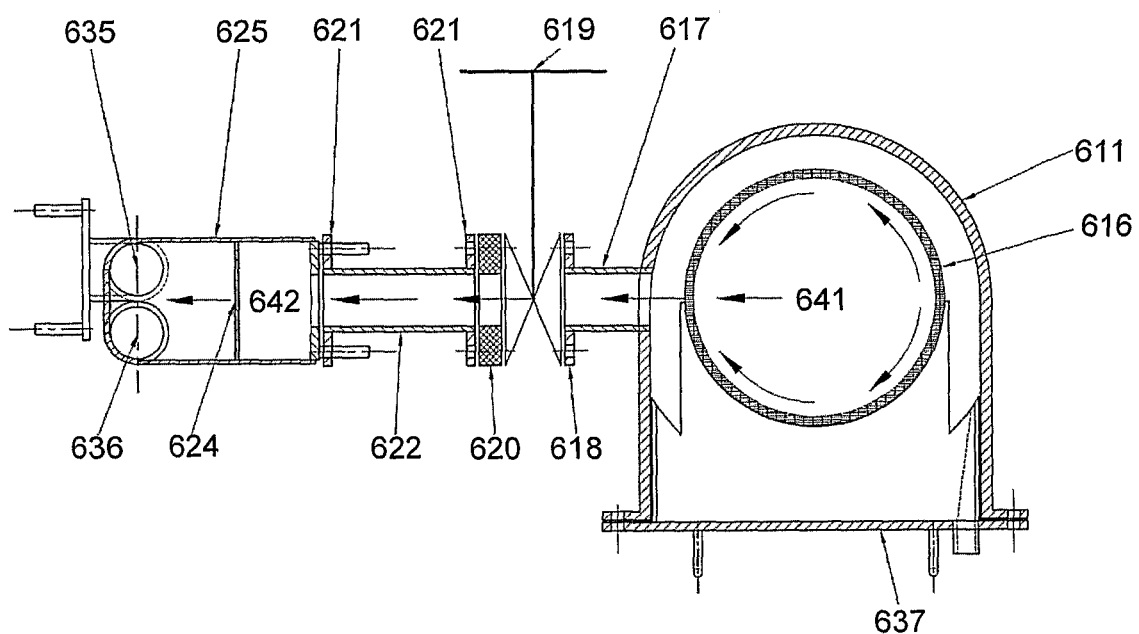

To help achieve this, as shown in FIG. 6B, adjustable orifice 632 and overflow pipe 636 can be coupled to the sensing tube 626. This allows an excess of material to be supplied to the sensing tube 626, to ensure the minimum level 643 is maintained, with any excess being drained, via the overflow pipe 636, to the collector 607, allowing it to be returned to the dense media sump 603.

In any event, the difference between the pressure measured by each of the sensors 629, 630, and the relative vertical height between the sensors 629, 630, can then be used to calculate a density, representative of the density of the slurry in the pipes 601, 602.

In this regard, the relationship between the measured density and the density of the slurry in the pipes 601, 602 may not be a one-to-one relationship due to a number of factors, such as the difference in pressure in the pipes 601, 602, and the sensing tube 626, as well as the size of material sampled by the media sampler 608. However, any such relationship can be determined, either by measurement or calculation, allowing the pressure in the pipes 601, 602 to be accurately determined.

Accordingly, the above described system allows material to be sampled from a flow pipe, to thereby allow properties of the material to be sensed, such as the material density. However, it will be appreciated that this may be used to measure a wide range of material properties by use of suitable sensing system other than the measuring device 109.

It will also be appreciated that the device can be used for measuring any material formed as a particulate suspension, and is not restricted to use with slurries, or to applications such as coal washeries.

It will be appreciated however, that use of the apparatus in the above described arrangement is particularly advantageous as it allows accurate density measurements to be in the feed pipe of a hydro cyclone, allowing the cyclone to be controlled with a high degree of accuracy, which is not otherwise possible with existing mechanical means.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. Apparatus for use in measuring properties of media formed from a particulate suspension, the apparatus including:
    a media sampler coupled to feed pipes to allow media flowing therethrough to be sampled, wherein the media sampler includes an element having a plurality of apertures to allow media to flow therethrough whilst restricting particulate material to flow therethrough, wherein each aperture is an elongate slot which extends in a direction which is substantially parallel to the flow of the media through the feed pipes; and
    a connector for coupling the media sampler to a sensor for sensing properties of the sampled media, wherein the connector includes a pressure reducing outlet for reducing a flow pressure of the sampled media flowing therethrough to the sensor.

2. Apparatus according to claim 1, wherein the media sampler includes:
    a jacket coupled to the feed pipes; and
    an outlet in fluid communication with the connector wherein the element is arranged within the jacket such that as media flows therethrough, at least some of the media passes through the plurality of apertures and into the outlet.

3. Apparatus according to claim 1, wherein the elongate slots have a width of at least one of:
    a) less than 2 mm;
    b) approximately 1 mm; and
    c) approximately 0.5 mm.

4. Apparatus according to claim 1, wherein the media sampler is provided in line with the feed pipes.

5. Apparatus according to claim 1, wherein a shape of the element matches a shape of the feed pipes.

6. Apparatus according to claim 2, wherein the element is shaped to ensure even flow of the particulate suspension through the media sampler.

7. Apparatus according to claim 2, wherein the element and one of the feed pipes are substantially cylindrically shaped.

8. Apparatus according to claim 7, wherein an inside diameter of the element is substantially the same as an inside diameter of the respective feed pipe.

9. Apparatus according to claim 2, wherein the jacket includes an access door to allow the element to be removed from the jacket.

10. Apparatus according to claim 1, wherein the pressure reducing outlet is configured to:
    provide a quiescent or laminar flow of sampled media to the sensor; and
    inhibit material blocking a surface of the element.

11. Apparatus according to claim 1, wherein the pressure reducing outlet reduces the pressure of the sampled media to substantially atmospheric pressure.

12. Apparatus according to claim 1, wherein the pressure reducing outlet is formed from one or more baffles defining a convoluted flow path.

13. Apparatus according to claim 1, wherein the connector includes a valve for selectively controlling the flow of sampled media.

14. Apparatus according to claim 1, wherein the sensor is a differential pressure sensor arrangement.

15. Apparatus according to claim 14, wherein the differential pressure sensor arrangement includes:
- a sensing tube having an inlet in fluid communication with the connector, wherein the sensing tube receives a constant flow of sampled media from the feed pipes;
- a return outlet for returning sampled media to a media source; and
- sensor system positioned along the sensing tube to thereby determine the pressure of the constant flow of sampled media at different positions.

16. Apparatus according to claim 15, wherein the differential pressure sensor arrangement further includes an overflow pipe for returning excess sampled media.

17. Apparatus according to claim 15, wherein the differential pressure sensor arrangement further includes a chamber which is coupled to the sensing tube and the connector.

18. Apparatus according to claim 17, wherein the chamber includes:
- a first outlet in fluid communication with the sensing tube; and
- a second outlet in fluid communication with an overflow pipe.

19. Apparatus according to claim 18, wherein the first and second outlets are relatively positioned such that sampled media only flows through the second outlet when overflow occurs.

20. Apparatus according to claim 1, wherein the particulate suspension is a slurry.

21. Apparatus for use in measuring properties of media formed from a particulate suspension, the apparatus including:
- a media sampler, the media sampler being coupled to feed pipes to allow media flowing therethrough to be sampled; and
- a connector for coupling the media sampler to a sensor arrangement for sensing properties of the sampled media, wherein the sensor arrangement includes:
  - a sensing tube having an inlet coupled to the connector, wherein the sensing tube receives a constant flow of sampled media from the feed pipes;
  - an outlet for returning sampled media, wherein the outlet is an adjustable orifice; and
  - a differential pressure sensor positioned along the sensing tube to thereby determine the pressure of the constant flow of sampled media at different positions.

22. Apparatus for use in measuring properties of media formed from a particulate suspension, the apparatus including:
- a media sampler, the media sampler being coupled to feed pipes to allow media flowing therethrough to be sampled, wherein the media sampler includes:
  - a jacket coupled to the feed pipes;
  - an outlet; and
  - an element having one or more apertures, the element being arranged within the jacket such that as media flows therethrough, at least some of the media passes through the one or more apertures and into the outlet; and
- a connector for coupling the media sampler to a sensor arrangement for sensing properties of the sampled media;
wherein a shape of the element matches a shape of the feed pipes.

23. Apparatus according to claim 22, wherein the element and the feed pipes have a substantially cylindrical shape.

24. Apparatus according to claim 23, wherein an inside diameter of the element is substantially the same as an inside diameter of the feed pipes.

25. Apparatus according to claim 21, wherein the differential pressure sensor system includes at least two pressure sensors.

26. Apparatus according to claim 1, wherein the pressure reducing outlet is in the form of an orifice.

27. Apparatus according to claim 1, wherein the pressure reducing outlet is formed from a plate including one or more apertures.

28. Apparatus according to claim 22, wherein the connector includes a pressure reducing outlet for reducing a flow pressure of the sampled media flowing therethrough to the sensor.

29. Apparatus according to claim 28, wherein the pressure reducing outlet is in the form of an orifice.

30. Apparatus according to claim 28, wherein the pressure reducing outlet is formed from a plate including one or more apertures.

31. Apparatus according to claim 15, wherein the sensing tube is provided in a substantially vertical orientation.

32. Apparatus according to claim 21, wherein the sensing tube is provided in a substantially vertical orientation.

33. Apparatus according to claim 1, wherein the element is provided in line with the feed pipes.

34. Apparatus according to claim 1, wherein the element includes a surface including the plurality of apertures, wherein the surface defines a first opening and a second opening, wherein the media flowing through one of the feed pipes enters the element via the first opening such that a portion of the media is sampled by flowing through the plurality of apertures whilst an unsampled portion of the media exits the element via the second opening and into another of the feed pipes.

35. Apparatus for use in measuring properties of media formed from a particulate suspension, the apparatus including:
- a media sample coupled to feed pipes to allow media flowing therethrough to be sampled, wherein the media sampler includes an element having a plurality of apertures to allow media to flow therethrough whilst restricting particulate material to flow therethrough; and
- a connector for coupling the media sampler to a sensor for sensing properties of the sampled media, wherein the connector includes a pressure reducing outlet for reducing a flow pressure of the sampled media flowing therethrough to the sensor;
wherein the media sampler includes:
  - a jacket coupled to the feed pipes; and
  - an outlet in fluid communication with the connector wherein the element is arranged within the jacket such that as media flows therethrough, at least some of the media passes through the plurality of apertures and into the outlet.

36. Apparatus for use in measuring properties of media formed from a particulate suspension, the apparatus including:
- a media sample coupled to feed pipes to allow media flowing therethrough to be sampled, wherein the media sampler includes an element having a plurality of apertures to allow media to flow therethrough whilst restricting particulate material to flow therethrough; and
- a connector for coupling the media sampler to a sensor for sensing properties of the sampled media, wherein the connector includes a pressure reducing outlet for reducing a flow pressure of the sampled media flowing therethrough to the sensor;
- wherein the pressure reducing outlet is configured to provide a quiescent laminar flow of sampled media to the sensor and inhibit material blocking a surface of the element.

37. Apparatus for use in measuring properties of media formed from a particulate suspension, the apparatus including:
- a media sample coupled to feed pipes to allow media flowing therethrough to be sampled, wherein the media sampler includes an element having a plurality of apertures to allow media to flow therethrough whilst restricting particulate material to flow therethrough; and
- a connector for coupling the media sampler to a sensor for sensing properties of the sampled media, wherein the connector includes a pressure reducing outlet for reducing a flow pressure of the sampled media flowing therethrough to the sensor;
- wherein the pressure reducing outlet reduces the pressure of the sampled media to substantially atmospheric pressure.

38. Apparatus for use in measuring properties of media formed from a particulate suspension, the apparatus including:
- a media sample coupled to feed pipes to allow media flowing therethrough to be sampled, wherein the media sampler includes an element having a plurality of apertures to allow media to flow therethrough whilst restricting particulate material to flow therethrough; and
- a connector for coupling the media sampler to a sensor for sensing properties of the sampled media, wherein the connector includes a pressure reducing outlet for reducing a flow pressure of the sampled media flowing therethrough to the sensor, wherein the sensor is a differential pressure sensor arrangement.

* * * * *